US007015025B2

(12) United States Patent
Honda et al.

(10) Patent No.: US 7,015,025 B2
(45) Date of Patent: Mar. 21, 2006

(54) PROCESS FOR PRODUCING VIRAL RNA POLYMERASE

(75) Inventors: Ayae Honda, Sizuoka (JP); Akira Ishihama, Mishima (JP)

(73) Assignee: Japan Science and Technology Agency, Saitama (JP)

( * ) Notice: Subject to any disclaimer, the term of this patent is extended or adjusted under 35 U.S.C. 154(b) by 138 days.

(21) Appl. No.: 10/399,478

(22) PCT Filed: Sep. 27, 2001

(86) PCT No.: PCT/JP01/08476

§ 371 (c)(1),
(2), (4) Date: Apr. 18, 2003

(87) PCT Pub. No.: WO02/33098

PCT Pub. Date: Apr. 25, 2002

(65) Prior Publication Data

US 2004/0126753 A1 Jul. 1, 2004

(30) Foreign Application Priority Data

Oct. 19, 2000 (JP) ............................ 2000-319156

(51) Int. Cl.
*C12N 7/04* (2006.01)

(52) U.S. Cl. ..................... 435/236; 435/69.1; 435/239; 435/320.1

(58) Field of Classification Search ............... 435/69.1, 435/320.1, 236, 239
See application file for complete search history.

(56) References Cited

FOREIGN PATENT DOCUMENTS

| | | |
|---|---|---|
| JP | 9-121867 | 5/1997 |
| JP | 11-199489 | 7/1999 |

OTHER PUBLICATIONS

Gal-on et al., Arch Virology 2000 vol. 145, pp. 37-50.*
Makoto Kobayashi, et al, "Reconstitution of influenza virus RNA polymerase from three subunits expressed using recombinant baculovirus system," Virus Research, vol. 22, 1992, pp. 235-245.
M. Kobayashi, et al, "Influenza virus PB1 protein is the minimal and essential subunit of RNA polymerase," Arch. Virol, vol. 141, 1996, pp. 525-539.
Licia Tomei, et al, "Biochemical characterization of a hepatitis C virus RNA-dependent RNA polymerase mutant lacking the C-terminal hydrophobic sequence," Journal of General Virology, vol. 81, 2000, pp. 759-767.
A. Gal-On, et al, "Characterisation of genetically modified cucumber mosaic virus expressing histidine-tagged 1a and 2a proteins," Arch. Virol., vol. 145, 2000, pp. 37-50.
Timothy Smith, et al, "Purification and Characterization of the Human Recombinant Histidine-Tagged Prostaglandin Endoperoxide H Synthases-1 and -2," Archives of Biochemistry and Biophysics, vol. 375, No. 1, 2000, pp. 195-200.
Tetsuya Toyoda, et al, "Molecular assembly of the influenza virus RNA polymerase: determination of the subunit-subunit contact sites," Journal of General Virology, vol. 77, 1996, pp. 2149-2157.
Ayae Honda, et al, "Purification and Molecular Structure of RNA Polymerase from Influenza Virus A/PR8[1]," J. Biochem, vol. 107, 1990, pp. 624-628.
Tetsuo Miyamura, "Properties of HCV nonstructural protein," Annual research report for the 9$^{th}$ year of the Heisei era. 1997.
Hwang et al., "Expression of Functional Influenza Virus RNA Polymerase in the Methylotrophic Yeast *Pichia pastoris*, " Journal of Virology, 2000, pp. 4074-4084, vol. 74, No. 9, American Society for Microbiology, Washington, D.C.
Honda et al., "Differential Roles of Viral RNA and cRNA in Functional Modulation of the Influenza Virus RNA Polymerase," Journal of Biological Chemistry, 2001, pp. 31179-31185, vol. 276, No. 33, The American Society for Biochemistry and Molecular Biology, Inc., Baltimore, MD.

* cited by examiner

*Primary Examiner*—James Housel
*Assistant Examiner*—Myron G. Hill
(74) *Attorney, Agent, or Firm*—Drinker Biddle & Reath LLP

(57) ABSTRACT

This invention relates to a method for producing virus RNA polymerases of RNA viruses, more specifically, virus RNA polymerases of RNA viruses free of virus genomic RNA.

Figure 1:
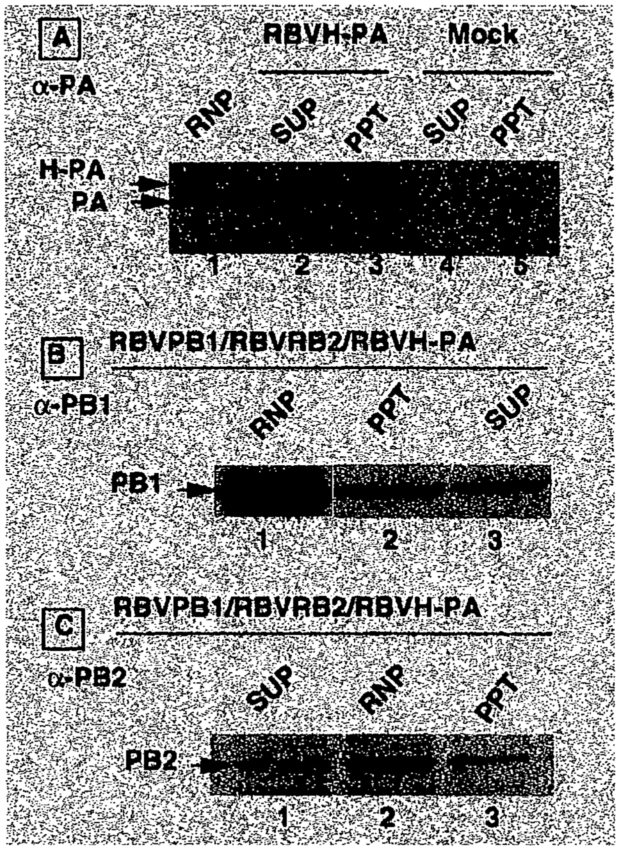

The methods described in this invention includes the procedures for preparation of cDNAs for the genes for the component proteins of RNA polymerase of an RNA virus, incorporation of the cDNA into baculovirus genome to construct recombinant virus, and the infection of insect cells with the recombinant virus to express RNA polymerase. In this method, it is recommended that all species of the recombinant viruses, each of which is designed for expressing each of the above-mentioned component protein genes of RNA polymerase, are coinfected into insect cells. Thus, cDNA is prepared for each of the component proteins of RNA polymerase and incorporated into baculovirus genome to construct recombinant virus for independently expressing the corresponding protein. In addition, the RNA viruses described above include influenza virus especially. In this method, RNA polymerase may be tagged to facilitate the subsequent purification. Furthermore, the tagged RNA polymerase described above may be purified using an adsorbent to trap the RNA polymerase at the tag. Another subject matter of this invention is to artificially prepare a complex of the component proteins of RNA polymerase of an RNA virus, or, in other words, to prepare RNA polymerase free from RNA virus genomic RNA. The RNA viruses described here include influenza virus, and the component proteins of RNA polymerase include PA, PB1 and PB2.

1 Claim, 3 Drawing Sheets

PROCESS FOR PRODUCING VIRAL RNA POLYMERASE

The application is a National Stage entry of PCT/JP01/08476, filed Sep. 27, 2001 which claims priority to Japan 2000-319156, filed Oct. 19, 2000.

1. Technical Field

This invention relates to a method for producing virus RNA polymerases of RNA viruses, more specifically, a method for producing virus RNA polymerases of RNA viruses isolated from virus genomes.

2. Prior Art

Conventional technology related to influenza virus RNA polymerase has focused on the development of methods to purify the polymerase from virus particles. Purification of the polymerase is important because influenza virus RNA polymerase can be regarded as an ultimate target for antiviral agents. From a more basic scientific viewpoint, influenza virus RNA polymerase is an interesting material in terms of the origin of its biologic evolution because, unlike DNA-dependent RNA polymerase, the RNA-dependent polymerase is considered to be involved in the proliferation of RNA genome. Despite considerable efforts, no method for efficient purification of the RNA polymerase tightly bound to viral genomic RNA has been established to date.

Previously, we collected a complex of RNA polymerase which was bound to genomic RNA by the centrifugation of virus particles in a high concentration of cesium chloride solution. Moreover, we successfully dissociated the RNA polymerase-RNA complex and released both RNA polymerase and RNA in a cesium trifluoroacetate solution used by centrifugation. The RNA polymerase, however, was found to be significantly inactivated during the purification process. Thus, this method was found to be inapplicable in large-scale purifications of the RNA polymerase.

In the subsequent study, three kinds of P proteins were purified and mixed together in a test tube to reconstitute the RNA polymerase. In a similar study, Summers and his colleagues of a U.S research group utilized SDS polyacrylamide gel electrophoresis (PAGE) to separate and purify these proteins. They have reported that a reconstituted system of the purified proteins showed an RNA synthesizing activity although the activity was only limited. In our study, we purified the three kinds of P proteins separately from cells infected with baculovirus and then reconstituted RNA polymerase with these proteins in vitro. Similar to the study conducted by Summers and his colleagues, we were able to confirm that the reconstituted system showed only a limited activity. Thus, this method also appeared to be inapplicable for large-scale production of RNA polymerase, and no other promising methods for this purpose are available to date. (Honda, A., Mukaigawa, J., Yokoiyama, A., Kato, A., Ueda, S., Nagata, K., Krystal, M., Nayak, D., and Ishihama, A Purification and molecular structure of RNA polymerase from influenza virus A/PR8. J. Biochem. 107, 624–628 (1990) and Kobayashi, M., Tuchiya, K., Nagata, K., and Ishihama, A.: Reconstitution of influenza virus RNA polymerase from three subunits expressed using recombinant baculovirus system. Virus Res. 22, 235–245(1992)).

On the other hand, Publication of unexamined Japanese Patent Application (Kokai) No. 9-121867 and Publication of unexamined application (Kokai) No. 11-199489 describe oligoribonucleotides as antiviral agents inhibiting protein expression induced by influenza virus. However, these oligoribonucleotides have been unsuccessful in proving their antiviral efficacy because of the difficulty in purification of the RNA polymerase.

Problems to be Resolved by the Invention

Conventional methods are available for isolating RNA polymerase directly from viruses. The content of the polymerase in a virus particle is so low that it is difficult to purify the polymerase and to remove undesirable contaminants by any of the conventional methods. Moreover, RNA polymerase in a small amounts tends to undergo rapid inactivation. Therefore, no practical methods are currently available for purification and isolation of functional RNA polymerase.

Means to Solve the Problems

Viruses are parasitic to a host which then provides most of the substances required for the virus growth. Viruses, themselves, produce only protein components of the virus genome and the virus particle according to their own gene information. Genomes exist as DNA in all living organisms, but RNAs in many viruses. Therefore, a virus cannot use the replication system of the host to replicate the genome and needs its own RNA replication system (RNA polymerase). One critical requirement for an antiviral agents is not to have any ill effects on the survival and growth of the host. For this reason, together with the fact that RNA polymerase is the sole enzyme synthesized by RNA viruses, RNA polymerase has been considered as the target for which antiviral agents should be developed. The strategy of aiming development of an antiviral agent targeting the RNA polymerase has so far been unsuccessful because, to date no effective methods have been established for isolation or production of a virus RNA polymerase preparation which is the prerequisite for such development. Our invention provides a method for dealing with such problems and introduces a new stage of development of antiviral agents.

The main subject of this invention is to provide a new method for producing a virus RNA polymerase comprising the steps of preparing cDNAs for the genes for the component proteins of an RNA polymerase of RNA virus, integrating said cDNAs into a baculovirus genome to construct recombinant viruses, infecting insect cells with said recombinant viruses, and expressing said cell to obtain RNA polymerase. Using this method, it is preferred that cDNAs each for the genes for the component proteins of an RNA polymerase of a virus are prepared, and said each cDNAs are integrated into each baculovirus genome respectively to construct recombinant viruses, and one insect cell is infected with all kinds of recombinant viruses. The RNA virus is preferably influenza virus. In this method, RNA polymerase may be tag-labeled to facilitate the subsequent purification. Furthermore, the RNA polymerase may be purified by using an adsorbent to trap the tagged RNA polymerase.

Another subject of this invention is an complex, which is artificially produced, consisting of the component proteins of an RNA polymerase of RNA virus, existing isolated from RNA virus genomic RNA. The RNA virus is preferably influenza virus and the component proteins of RNA polymerase may be PA, PB1 and PB2.

BRIEF DESCRIPTIONS ON THE DRAWINGS

FIG. 1 shows the P proteins of influenza virus expressed in insect cells infected with recombinant baculovirus.

[FIG. 1A] Sf9 cells were infected with recombinant baculovirus RBVH-PA (baculovirus having the gene for His-tagged PA protein (H-PA)) at a moi (multiplicity of infection) of 2. After a 4-day culture, the cells were harvested and processed to prepare a cell lysate. The cell lysate was centrifuged at 2,000 rpm for 5 min. The resulting supernatant (SUP or cytoplasm fraction) and the precipitate (PPT or nucleus fraction) were fractionated by SDS PAGE. The gel was subjected to immuno-blotting (Western blot) using anti-PA antibodies.

[FIGS. 1B and C] Sf9 cells were coinfected with three species of recombinant baculoviruses (RBVPB1, RBVPB2, and RBVH-PA) at a moi (multiplicity of infection) of 2 for each virus. After a 4-day culture, the cells were harvested and processed as described above. Both cytoplasm and nucleus fractions were immuno-blotted with anti-PB1[B] or anti-PB2[C] antibodies.

Figure 2:
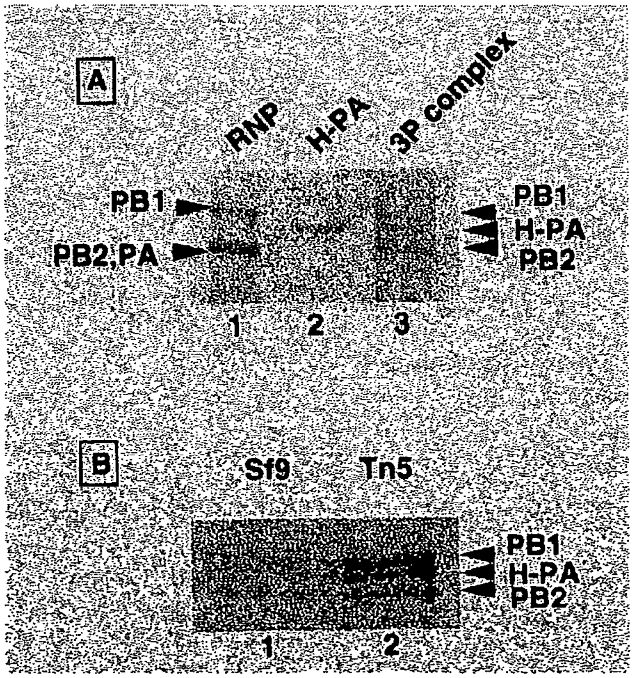

FIG. 2 shows the purification of the 3P complex from insect cells infected with recombination baculovirus.

[FIG. 2A] Tn5 cells were infected with recombination baculovirus RBVH-PA (Lane 2) or with all three species of recombinant baculovirus (RBVPB1, RBVPB2, and RBVH-PA) at moi of 2 for each virus, and the cells were cultured for 4 days. The supernatant fractions (SUP) of whole cell lysate were mixed with metal affinity resin, and the imidazole eluates were fractionated by SDS-8% PAGE. The gels were stained with Coomassie brilliant blue (CBB). Lane 1, RNP isolated from influenza virus A/PR8; lane 2, the imidazole eluate fraction from RBVH-PA-infected cells; lane 3, the 3P complex isolated from cells coinfected with three species of recombinant baculovirus.

[FIG. 2B] Sf9 cells (lane 1) or Sn5 cells (lane 2) were coinfected with all three species of recombinant baculovirus. After a 4-day culture, the 3P complex was isolated and analyzed as described above.

Figure 3:
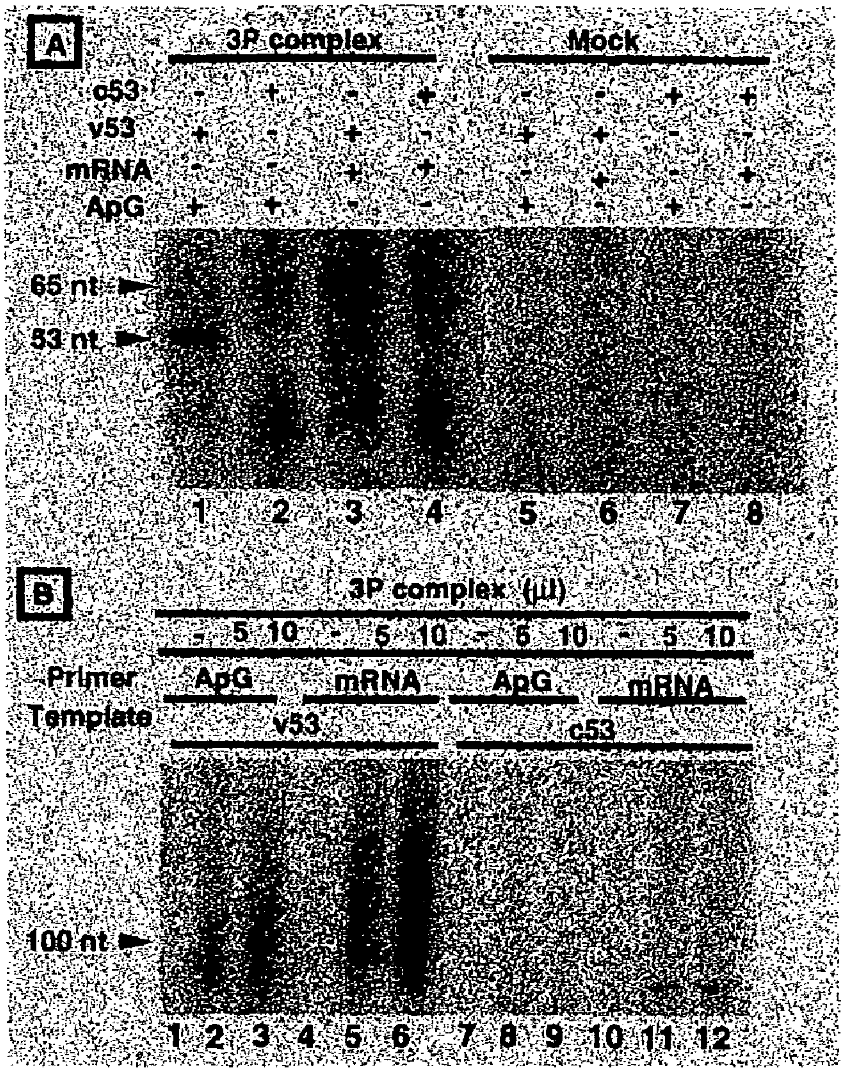

FIG. 3 shows model template-dependent RNA synthesis activity of the 3P complex.

[FIG. 3A] The 3P complex purified from the recombinant virus-infected cells or the corresponding fraction from mock-infected cells was examined in vitro for RNA synthesis activity in incubation in the presence of a template of v53 (lanes 1, 3, 5, and 6) or c53 (lanes 2, 4, 7, and 8) and a primer of ApG (lanes 1, 2, 5, and 7) or globin mRNA (lanes 3, 4, 6, and 8). The products were separated by urea-8% PAGE.

[FIG. 3B] RNAs synthesized by the 3P complex in the presence of the template, v53 (lanes 1–6) or v53 (lanes 7–12), and the primer, ApG (lanes 1–3 and 7–9) or globin mRNA (lanes 4–6 and 10–12), were mixed with an oligo $(dT)_{30}$ resin. The resin-bound RNAs were recovered and analyzed by urea-6% PAGE. The migration position of a marker RNA of 100 nucleotides (nt) long is shown on the left.

Figure 4:
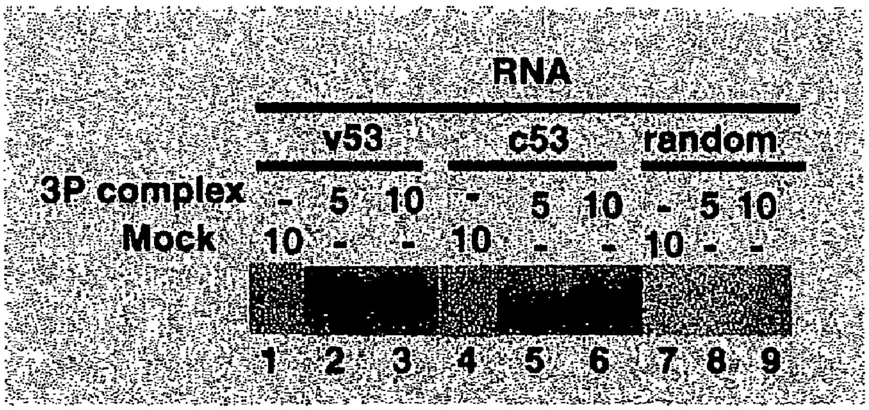

FIG. 4 shows template RNA-binding activity of the 3P complex.

The purified 3P complex was incubated with $^{32}P$-labeled v53 (lanes 1–3), c53 (lanes 4–6) or RNA with random sequence (lanes 7–9), and then irradiated with a UV lamp for cross-linking. The RNA-crosslinked proteins were analyzed by urea-8% PAGE, and the gel was exposed to X-ray film.

Figure 5:
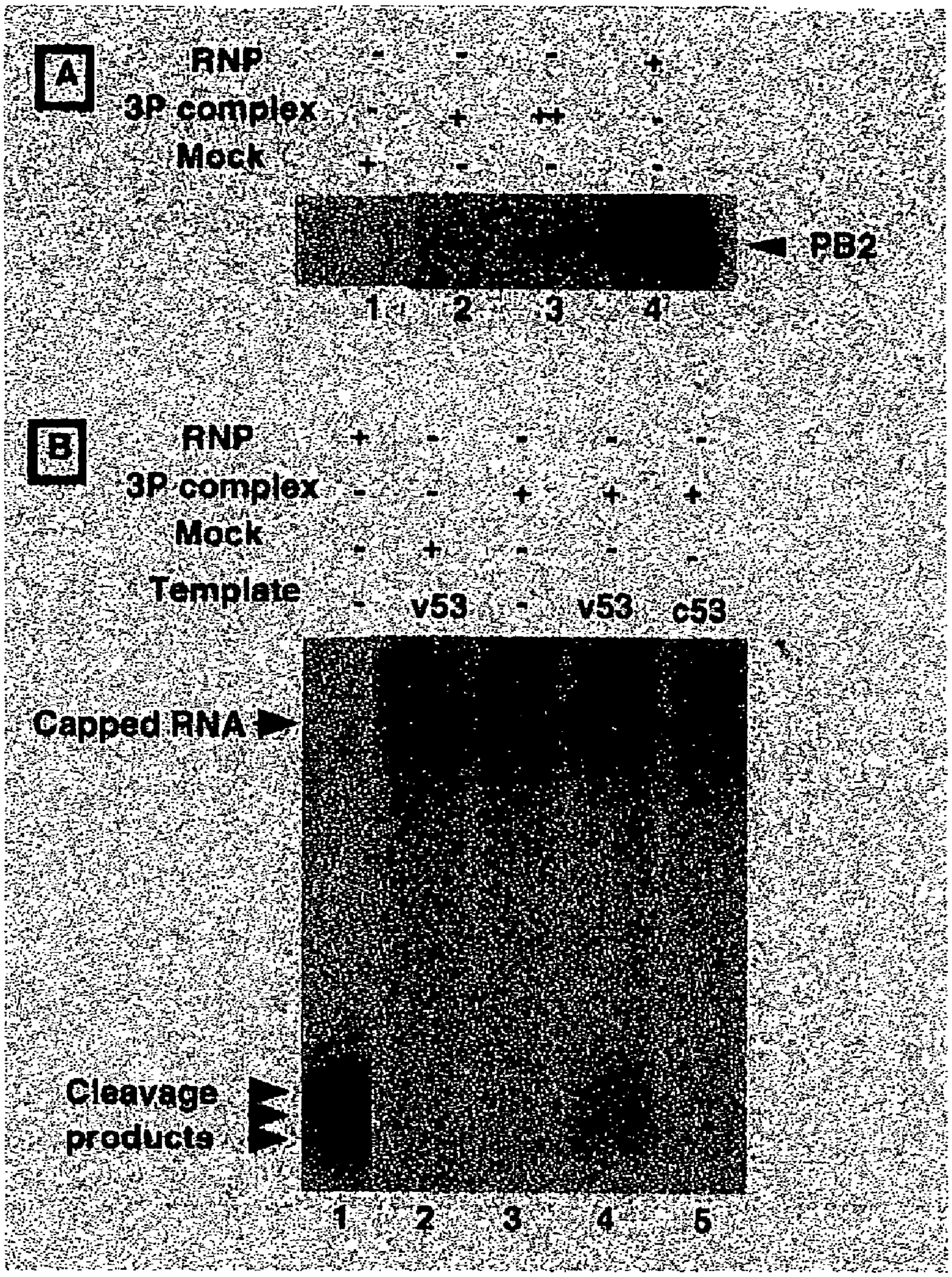

FIG. 5 shows capped RNA-binding and cleavage activities of the 3P complex.

[FIG. 5A] The purified 3P complex (12 pmol/ml or 3 $\mu$g/ml; lane 2, 5 $\mu$l; lane 3, 10 $\mu$l) and the isolated RNP (lane 4) were assayed for the capped RNA-binding activity. RNA with radioactivity of $^{32}P$ only at the capped position was mixed with the 3P complex or RNP and then irradiated with a UV lamp. After digestion with ribonuclease T1 and ribonuclease A, the RNA-cross-linked proteins were analyzed by urea-8% PAGE. The gel was exposed to X-ray film.

[FIG. 5B] RNP (lane 1), the 3P complex (lanes 2–4), and the corresponding fraction from mock-infected cells (lane 5) were assayed for the capped RNA endonuclease. Each fraction was mixed with capped poly(A) labeled with $^{32}P$ only at cap-1 in the absence of (lanes 1–2) or presence of either 1 pmole of v53 (lanes 3 and 4) or 1 pmole of c53 (lane 5) template at 30° C. for 30 min. The resulting incubation mixture was analyzed for RNA. The gel was exposed to an imaging plate overnight, and the plate was analyzed with a BAS2000 image analyzer (Fuji).

DESCRIPTION OF THE EMBODIMENTS

RNA viruses can be classified into two categories. RNA viruses of one category can synthesize RNA polymerase by encoding the genomic RNA and infecting the host. In other words, RNA viruses of this category can utilize the genome as the template (mRNA) in the protein synthesis, and thus are called "plus-strand RNA viruses". RNA viruses of the other category can not utilize the genome as the template in the protein synthesis, but transcribe the genomic information onto a complementary chain to use the chain as the mRNA. Thus, RNA viruses of this latter category are called "minus-strand RNA viruses". Host living organisms do not have any enzyme to catalyze transcription of the genomic RNA to complementary RNA. RNA viruses of this latter category, however, have RNA polymerase in the virus particle. RNA viruses of this latter category include those of Paramyxoviridae, Orthomyxoviridae, Rhabdoviridae, Bunyavirus, and Arenaviridae. This invention can be applied to production of RNA polymerase of all viruses of this category.

When this invention is applied to the production of RNA polymerase of the influenza virus, the procedures are as follows:

(1) Preparation of three species of recombinant baculoviruses, each of which independently expresses one of the subunits, PB1, PB2, and PA, of influenza virus RNA polymerase. cDNA for PB1 or PB subunit is incorporated into baculovirus genomic DNA by homologous recombination as follows. First, these cDNAs are incorporated into the intermediate vector of *E. coli* to confirm their expression in *E. coli* cells. These intermediate vector DNAs are introduced with the baculovirus DNA into host cells of an established insect cell strain by electroporation or the lipofectin method. Homologous recombination is induced in the cells, and the resulting transformed baculoviruses containing the genes for PB1 and PB2 are isolated. On the other hand, cDNA of the other subunit, PA, is introduced into a downstream region from a histidine (His) tag label (HAT) in the pHAT vector containing the HAT label to express the PA protein in a fused form with a sequence rich inHis residues at the N-terminal and thus to facilitate the purification of the RNA polymerase from the cells expressing the polymerase. This intermediate vector is inserted into baculovirus DNA by homologous recombination in a manner similar to that described above for insertion of PB1 and PB2.

(2) Reconstitution of Influenza Virus RNA Polymerase with its Three P Protein Subunits Simultaneously Expressed by Recombinant Baculoviruses-Infected Insect Cell System Insect cells are infected with three species of recombinant baculoviruses, each of which is constructed for expression of one of the three P protein subunits of influenza virus RNA polymerase. The expression of each subunit is confirmed by Western blot with the corresponding antibody (an immunoassay). The cells are homogenized with a homogenizer to prepare a nucleus fraction. Nuclei are treated with a detergent and centrifuged at 50,000 rpm for 2 hr. The resulting supernatant is mixed with TALON metal affinity resin (an adsorbent) to trap proteins labeled with a His tag. The resin adsorbing proteins are treated with 100 mM imidazole to reduce the interaction between the resin and the His tag and thus to elute the proteins. The eluate is fractionated by SDS PAGE to analyze the expressed P protein subunits by Western blotting. In this invention, PA alone is labeled with the His tag. Nevertheless, the eluate contains not only His tagged PA, but also PB1 and PB2. This indicates that the three P protein subunits are obtained as a complex form by the method described in this invention.

(3) Purification of the Influenza Virus RNA Polymerase Expressed in the Insect cell System and Measurement of its Activity A crude extract is obtained from a homogenate of recombinant baculovirus-infected insect cells. From the extract, reconstituted RNA polymerase is purified as described above. The purified specimen is fractionated by SDS PAGE. Proteins in the gel are stained with Coomassie blue to confirm the purity of the P proteins. The method described in this invention has confirmed to offer a purified preparation of functional P protein complex in terms of the following four activities:

(1) template RNA-dependent RNA synthesis activity
(2) primer-dependent RNA synthesis activity
(3) host-derived mRNA cap (cap-1) structure-recognizing and binding activity
(4) activity to cleave cap (cap1) structure-containing RNA at a specific site RNA polymerases of viruses in the categories described above in this invention can be produced by the method described above.

Pratical examples are shown below to demonstrate this invention, but not to restrict this invention to the examples.

EXAMPLES

The practical examples were carried out by using the following materials.

(i) Bac-to-Bac vector (GIBCO-BRL Inc.) for construction of recombination baculoviruses
(ii) Insect cells of established cell line (including Sf9 and Tn5) for expression of virus proteins
(iii) TALON metal affinity resin (CLONTECH Inc.) for purification of the proteins expressed by insect cells
(iv) Reagents for measurement of RNA polymerase activity The substrates for RNA synthesis (ATP, GTP, CTP, and UTP) (Pharmacia Inc.), and ApG and globin mRNA to be used as the primer (v) Reagents for preparing template RNA Vector pV53 for preparing template RNA and T7 RNA polymerase (TAKARA)

(vi) Reagents for measurement of capped RNA cleavage activity

Labeling agent for the RNA cap-site, [$\alpha$-$^{32}$P]GTP, and capping enzyme

Test Procedures

The insect cell lines established from *Spodoptera frugiperda* (Sf9) and *Trichoplusia ni* (Tn5) were used for infection with recombinant baculoviruses. *Autographa california* nuclear polyhedrosis virus (AcNPV) was used for construction of recombinant viruses.

Recombinant baculoviruses for expression of PB1 and PB2 were constructed as described in the previously published report (Kogayashi M., Tsuchiya K., Nagata K., and Ishihama A. (1992) Virus Res. 22 235–245). For the construction of recombinant virus for expression of PA, cDNA for PA was amplified by polymerase chain reaction (PCR) and inserted between the NcoI and BglII sites of pAcHLT-B (Phamigen). The resulting plasmid DNA (pAcHLTPA) was linearized and co-transfected with baculovirus DNA into Sf9 insect cells by the liposome method. After 72-hr culture at 27° C., the supernatant was harvested and the recombinant viruses contained in the supernatant were infected into Sf9 cells. The culture supernatant was harvested, and the titer of recombinant virus (RBVH-PA) was determined by the plaque assay. The titer of the virus preparation was $10^8$ PFU/ml.

Tn5 or Sf9 cells were coinfected with the three species of recombinant baculovirus at a moi of 2 for each. After a4-day culture for the co-infection, $10^8$ cells were collected from the culture and suspended in 5 ml of the cell disruption buffer, 10 mM HEPES buffer (pH 7.6) containing 10 mM KCl, 1.5 mM $MgCl_2$, 2 mM dithiothreitol (DTT), 0.1% TritonX-100 and 1 mM phenylmethylsulfonyl fluoride (PMSF, Sigma). The cells suspension was homogenized by using a Dounce homogenizer and centrifuged at 2,000 rpm for 5 min to recover nuclei. The nuclei were homogenized in 3 ml of the nucleus extraction buffer, 10 mM sodium phosphate buffer (pH 7.0) containing 500 mM NaCl and 20% glycerol. The homogenate was incubated with stirring in an ice bath for 30 min and then centrifuged at 40,000 rpm for 2 hr. The resulting supernatant (nucleus extract) was mixed with metal affinity resin (Clontech) and incubated for 1 hr at 4° C. with constant rotation. The resin was washed with the washing buffer, 50 mM sodium phosphate buffer (pH 7.0) containing 300 mM NaCl and 5 mM imidazole until UV monitoring of the eluate showed no detectable proteins in the eluate. The resin was then eluted with the elution buffer containing 100 mM imidazole. The eluted proteins were analyzed by SDS-8% PAGE, and the gels were stained with Coomassie brilliant blue (CBB).

The P proteins separated by SDS-PAGE were electro-blotted onto PVDF membranes in 10 mM CAPS buffer (pH 11) containing 10% methanol. The blotted filters were incubated with anti-PA, anti-PB1, and anti-PB2 antibodies for 1 hr at 37° C. and then with peroxidase-conjugated anti-rabbit IgG. The peroxidase activity was visualized by the reaction with 3,3'-diaminobenzidine tetrahydrochloride (DAB) (DOJIN) to detect the P proteins. The anti-P protein antibodies used in the detection of the expressed P proteins had been raised in rabbits against the purified P proteins over expressed in the culture of *E. coli* cells.

RNA synthesis was carried out for 60 min at 30° C. in 50 $\mu$l of a standard reaction mixture in 50 mM HEPES/KOH buffer (pH 7.6) containing 100 mM NaCl, 5 mM magnesium acetate, 2 mM DTT, 0.25 mM each of ATP, GTP, and CTP, 4 $\mu$M UTP, 10 $\mu$Ci [$\alpha$-$^{32}$P]UTP, 0.25 mM ApG or 250 ng globin mRNA, 1 unit RNasin (Promega), and 1 pmol of v53 or c53 model RNA template. The transcripts were analyzed by 10% PAGE in the presence of 7M urea. The gels were exposed to imaging plates and then analyzed with a BAS2000 image analyzer (Fuji). The model templates (v53 and c53) were synthesized by transcribing pV53 or pC53 plasmid DNA using T7 RNA polymerase.

Radioactive vRNA and cRNA were synthesized by transcribing pV53 and pC53 DNA, respectively, by using T7 RNA polymerase in the presence of radioactive substrates. In an RNA-binding reaction mixture of 50 mM HEPES/KOH buffer (pH 7.8) containing 100 mM NaCl, 5 mM magnesium acetate, 2 mM DTT, and 10 $\mu$g tRNA, 10 $\mu$l of the 3P complex (a complex consists of 3 species of protein) and 10,000 cpm of radioactive v53, c53 or random RNA (TMV 3'-terminal sequence) were incubated in a final volume of 50 $\mu$l for 30 min at 30° C. The reaction mixture was irradiated with a UV lamp for 30 min. After the addition of anti-PB1, the mixture was further incubated at 37° C. for 1 hr. The mixture was incubated with protein A-Sepharose (Pharmacia) for 2 hr in an ice bath to recover the resulting antigen-antibody immunocomplexes as protein A-Sepharose complexes. The protein A-Sepharose complexes were washed once with PBS and then subjected to SDS-8% PAGE. The gels were analyzed as described above.

Cross-linking of capped RNA to the P proteins was carried out as described in the previously published report (Honda A., Mizuno K., and Ishihama A. (1998) Virus Res. 55 199–206). In brief, globin mRNA was decapped and recapped for one cycle by treating with vaccinia virus guanylyltransferase (Gibco BRL) in the presence of [$\alpha$-$^{32}$P] GTP. The recapped globin mRNA with a cap structure labeled with $^{32}$P (about 1,000 cpm) only at the 5'-position was incubated with the 3P complex or viral nucleoprotein (RNP) in 50 mM HEPES/KOH buffer (pH 7.6) containing 100 mM NaCl, 5 mM magnesium acetate, 2 mM DTT and 1 unit of RNasin (Promega) in a final volume of 50 $\mu$l at 30° C. for 30 min. The mixture was irradiated with a UV lamp for 30 min. The RNA-cross-linked proteins were digested with RNase A and RNase T1 and then incubated with anti-PB2 at 37° C. for 1 hr. The reaction mixture was incubated with protein A-Sepharose (Pharmacia) for 2 hr in an ice bath to precipitate the antigen-antibody immunocomplexes formed. The precipitate was washed once with phosphate buffered saline (PBS) and then fractionated on an SDS-8% gel by electrophoresis. The gel was analyzed as described above.

The purified 3P complex was incubated in 50 mM HEPES/KOH buffer (pH 7.8) containing 100 mM NaCl, 2 mM DTT, 0.3% Triton X-100, 0.25 mg/ml BSA, and capped globin mRNA or poly(A) (with a cap structure labeled with about 2,000 cpm of $^{32}$P only at the 5'-position) for 30 min at 30° C. in a final volume of 50 $\mu$l. The reaction products were extracted with phenol-chloroform, precipitated with ethanol, and analyzed by 12% PAGE in the presence of 7 M urea. The gel was analyzed as described above.

Oligotex $(dT)_{30}$ (Takara) was added to the reaction mixture. The reaction mixture was heated at 75° C. for 10 min. The heat-treated mixture was placed in an ice bath for 5 min, and 5 M NaCl was then added to the mixture to give a final concentration of 500 mM. The mixture was incubated at 37° C. for 10 min and then centrifuged at 2,000 rpm for 5 min. The precipitate was washed with 10 mM Tris-HCl buffer (pH 7.5) containing 1 mM EDTA, 0.5 M NaCl, and 0.05% SDS and resuspended in 0.1 ml of sterilized distilled water. RNA was extracted with phenol-chloroform, precipitated with ethanol, and then analyzed by PAGE in the presence of 7 M urea.

Test Results

For the expression of the three different P protein subunits of influenza virus RNA polymerase, recombinant baculoviruses were constructed using cDNAs for vRNA segments 1, 2, and 3, containing the genes for PB1, PA, and PB2 proteins, respectively. cDNA for PA was inserted into the pAcHLT vector to express the PA protein as a fused form with a histidine (His) tag sequence of 40 amino acids in length at its N-terminal. This procedure facilitated the purification of the resulting 3P complex. From the fact that the N-terminal sequence of PA was not involved in subunit-subunit contact, the addition of the His tag was presumed to have no inhibitory effects on the assembly and activity of RNA polymerase. The construction of recombinant baculoviruses for production of PB1 and PB2 was described in the previously published report (Kogayashi M., Tsuchiya K., Nagata K., and Ishihama A. (1992) Virus Res. 22 235–245).

To confirm the expression of the P proteins, recombinant baculoviruses were infected into Sf9 cells under various conditions, and the whole cell lysates were analyzed by immunostaining with specific polyclonal antibodies against each P protein. In the case of Sf9 cells infected with the recombinant baculovirus RBVH-PA alone, a band showing a cross reaction with anti-PA was detected in both cytoplasm and nucleus fractions by SDS-8% PAGE (FIG. 1A, lanes 2 and 3). The migration of H-PA (His-tagged PA) was slightly slower than that of authentic PA without His-tag (FIG. 1A, lane 1). The immunostaining detected no bands in the extracts of mock-infected cells (FIG. 1A, lanes 4 and 5). Sf9 cells infected with the recombinant baculovirus RBVH-P alone expressed neither PB 1 nor PB2. In the extract of Sf9 cells coinfected with all the three recombinant viruses, RBVPB1, RBVPB2, and RBVH-PA, the expression of PB1 and PB2 in addition to H-PA was demonstrated by immunostaining with anti-PB1 and anti-PB2 (FIGS. 1B and C). PB1 and PB2 were again recovered in both of the cytoplasm and nucleus fractions.

In order to examine whether the three viral P proteins form complexes in insect cells, Tn5 cells were coinfected with the three species of recombinant baculoviruses (at moi 2 for each virus). After the cell lysate was examined by SDS-8% PAGE, all three P proteins were detected by immunostaining with the corresponding antibodies. The majority of each was recovered mostly in the nucleus fraction (FIG. 1). To purify P protein complex, the nucleus extract was centrifuged at 40,000 rpm for 1 hr and the supernatant was directly subjected to metal affinity resin purification. The material eluted with 100 mM imidazole was fractionated by SDS-8% PAGE and the gel was stained with Coomassie brilliant blue (CBB). Three bands were detected (FIG. 2A, lane 3). These bands showed cross-reactivity with anti-PB1, anti-PA and anti-PB2 antibodies in the order of migration. SDS-PAGE showed that both PB1 and PB2 co-migrated with the corresponding P protein associated with viral RNP cores (FIG. 2A, lane 1). On the gel, the H-PA migrated as fast as the recombinant H-PA recovered from RBVH-PA virus-infected cells (FIG. 2A, lane 2), but more slowly than the RNP-associated untagged PA (FIG. 2A, lane 1). Thus we conclude that at least some of the PB1 and PB2 molecules are associated with His-tagged PA protein.

In order to construct a high-level expression system for these influenza virus P proteins we compared the levels of these proteins expressed in cells of two insect cell lines, Tn5 and Sf9, which were cultured under the same conditions at 27° C. After the purification by using a metal affinity resin, all three P proteins were detectable even by CBB staining of SDS-gel (FIG. 2B). From the staining intensity, it indicates that the 3P complex thus isolated contained the three P proteins in equal amounts. Since the level of the 3P complex expressed in the Tn5 culture was higher than in the Sf9 culture, Tn5 was used for purification of the 3P complex in a large scale. From the CBB staining intensity, the yield of the 3P complex was estimated to be about 5 $\mu$g from $1\times10^8$ virus-infected Tn5 cells.

The influenza virus RNA polymerase solubilized from viral RNP cores shows RNA synthesis activity if exogenously added model RNA templates which carry terminal conserved sequences of viral RNA segments. The RNA synthesis activity of the purified 3P complex was examined using two model templates (v-sense (minus-strand) v53 and c-sense (plus-strand) c53) and two alternative primers (globin mRNA and dinucleotide ApG). When v53 was used as a template, RNA products were detected in both ApG- and mRNA-primed reaction (FIG. 3A, lanes 1 and 3). One of the transcripts from the mRNA-primed reaction (lane 3) was longer than the ApG-primed transcript by about 12 nt (lane 1). The nucleus extract of mock-infected cells was unable to synthesize RNA from either template (FIG. 3A, lanes 5–8). These results indicate that the detected RNA synthesis is mediated by the 3P complex formed in insect cells infected with recombinant virus, but not by any cellular enzymes in the insect cells. Since the 3P complex is unable to synthesize any RNA when given RNA template with random sequences, this indicates that the 3P complex, similar to the native viral RNA polymerase, recognizes vRNA in a specific manner.

When c53 was used as template, RNA products were detected particularly in the presence of ApG primer (FIG. 3A, lane 2). The size of the major transcript from this cRNA-directed and ApG-primed reaction was, however, shorter than the 53 nt template. This was probably due to the internal initiation at an as yet unidentified ApG-binding site within the c53 RNA. The activity of globin mRNA-primed transcription was low, and no clear bands of transcripts were detected at least under the conditions employed (FIG. 3A, lane 4). These results indicate that only v-sense RNA may be able to direct capped RNA-primed transcription.

Influenza virus RNA polymerase is interconvertible between transcriptase and replicase, but the capped RNA-primed initiation of RNA synthesis is a unique characteristic of the transcriptase. On the other hands, the replicase form of RNA polymerase is considered to be involved in the initiation of de novo RNA synthesis without using primers because vRNA in virus particles retains 5'-triphosphate. The 3P complex purified from insect cells infected with recombinant baculovirus did not catalyze RNA synthesis in the absence of primers. Therefore, we propose that the 3P complex represents the transcriptase form of viral RNA polymerase.

Influenza virus RNA polymerase recognizes specific sequences located at 5'- and 3'-terminals conserved sequences of vRNA and cRNA, which act as transcription promoter and replication origin, and its bounding to these sequences exerts its intrinsic activity of enzyme. Accordingly, the binding of the 3P complex to vRNA and cRNA was examined. The 3P complex was incubated with a radio-labeled model templates, v53 and c53, and random RNA of a similar size at 30° C. for 30 min in the transcription assay mixture without substrates, then irradiated with a UV lamp for 30 min to promote cross-linking. Immediately after the UV irradiation, the mixture was subjected to RNase digestion. The digested products were immunoprecipitated with a combination of anti-PB 1 and protein A. The immunoprecipitates were analyzed by SDS-8% PAGE. Both vRNA (FIG. 4, lanes 2 and 3) and cRNA model templates were cross-linked to the 3P complex (FIG. 4, lanes 5 and 6), but random RNA (FIG. 4, lanes 8 and 9) was not. These results indicate that the 3P complex formed in insect cells, similar to the natural virus RNA polymerase, is able to specifically recognize both vRNA and cRNA.

One unique feature of influenza virus growth is that host cell capped RNA is used as a source of primers for initiation of viral transcription. Even more remarkably, the influenza virus RNA polymerase itself is able to cleave capped RNA at specific positions near the 5'-cap structure. Therefore, the finding that globin mRNA could serve as a primer for transcription by the 3P complex indicates that the 3P complex has both capped RNA binding and cleavage activities. To confirm this prediction, we examined next by the binding activity of 3P complex to capped RNA. For this purpose, rabbit globin mRNA recaped with [$\alpha$-$^{32}$P]GTP was prepared using vaccinia virus guanylyltransferase. The 3P complex or viral RNP was then incubated with recapped RNA (with $^{32}$P only at the cap-1 structure). Immediately after the incubation, the mixture was irradiated with a UV lamp for cross-linking. After subsequent digestion with RNase A and RNase T1, the 3P complex was immunoprecipitated with a combination of anti-PB2 serum and protein A, and the immuno-precipitates were analyzed by SDS-8% PAGE. The nucleus extract from mock-infected cells produced no radioactive bands at the P protein positions (FIG. 5A, lane 1). Both of the 3P complex (FIG. 5A, lanes 2 and 3) and RNP (FIG. 5A, lane 4), however, revealed $^{32}$P radioactivity at the position corresponding to the PB2 band. These results suggest that the 3P complex possesses the capped RNA-binding activity. In the products extracted from insect cells infected with recombinant baculovirus, radioactivity was also detected in at least one additional band migrating faster than PB2. This band, however, was also detected in the nucleus extract from mock-infected cells, indicating that it corresponds to a fast migrating host (insect cells) protein having a binding activity to the capped RNA.

Next, we examined for its capped RNA cleavage activity, using the purified 3P complex. In this experiment, both globin mRNA and capped poly(A), both with $^{32}$P only at the cap-1 structure, were used as the substrates. Capped poly (A) is a good substrate for endonucleolytic cleavage by RNP. As expected, incubation with RNP resulted in cleavage of the capped poly(A) into fragments of 10–13 nts in length (FIG. 5B, lane 1). The capped RNA was also cleaved by the purified 3P complex in the presence of v53 template (FIG. 5B, lane 4), but not in the absence of template RNA (FIG. 5B, lane 3). No cleavage of the capped RNA was also observed with the corresponding extract from mock-infected cells (FIG. 5B, lane 2). It has been previously observed that capped RNA endonuclease associated with RNA polymerase is activated via binding to the template RNA (Hagen, M., Chung, T. D., Butcher, J. A., and Krystal, M. (1994) J. Virol. 68, 1509–1515; Li, M. L., Ramirez, B. C., and Krug, R. M. (1998) EMBO J. 17, 5844–5852). To our surprise, however, the enhancement of capped RNA endonuclease was observed only with v53 template. c53 was virtually inactive in the activity this regulatory function of RNA polymerase activation (FIG. 5B, lane 5). These results demonstrate for the first time that the 3P complex discriminates between v-sense and c-sense RNAs.

If the 3P complex formed in insect cells possesses the catalytic activity as a transcriptase, these may include an activity of polyadenylation coupled to vRNA transcription. To test this possibility, globin mRNA-primed vRNA-transcription products were characterized in detail. Analysis of the RNA products by 10% PAGE revealed diffuse radioactive bands above the 65-nt-long transcript. To examine whether these slowly migrating RNAs carry poly(A) sequences added to the newly synthesized RNA, in vitro transcripts were mixed with an oligo(dT)$_{30}$ resin, and the resin-bound RNA was eluted by heat-treatment in the presence of high concentrations of salt to eluted RNAs. The eluate was analyzed by 6% PAGE in the presence of 7 M urea. As shown in FIG. 3B, a radioactive RNA was detected, which migrated more slowly than a size marker of about 100 nt in length. The average size of oligo(dT)$_{30}$-bound RNAs was greater for mRNA-primed transcripts (FIG. 3B, lanes 5 and 6) than for ApG-primed transcripts (FIG. 3B, lanes 2 and 3). These results indicate that at least some of the RNA products formed on the vRNA model template in the presence of either ApG or mRNA primers contain poly(A)

sequences. On the other hand, most of the cRNA-directed transcripts did not bound to the oligo$(dT)_{30}$ resin. After treatment of the vRNA transcripts with RNase A and RNase T1, some nuclease-resistant RNA moieties were detected by gel electrophoresis. These moieties were most likely to be poly(A) sequences. Such polyadenylation of vRNA-directed transcripts is another characteristic and unique function associated with the transcriptase.

Advantageous Effect of the Invention

Efforts to establish prevention and treatments of influenza have been focused mainly on the development of the immuno-therapy using the antigens against the whole particles or a component protein(s) of the virus and the exploratory studies on agents to interfere with physiological functions of the components of the virus. Among the targets examined in such efforts, the only target left is RNA polymerase. The method for RNA polymerase production in a large-scale established in this invention provides the base for the mass-screening of inhibitors of RNA polymerases and drug discovery from substrate analogues for the RNA polymerase-mediated reactions. Moreover, RNA polymerase production facilitates the protein structure identification of RNA polymerases and even further drug discovery based on the identified structures.

What claimed is:

1. A method for producing an RNA polymerase of influenza virus comprising the steps of:

preparing three cDNAs, each cDNA encoding a component protein of an RNA polymerase of influenza virus, wherein said proteins are PA, PB1 and PB2 and the PA of said RNA polymerase is tag-labeled at the N-terminal;

integrating each of said cDNAs into a separate baculovirus genome to construct three kinds of recombinant viruses;

infecting an insect cell with each kind of recombinant virus;

expressing said cDNAs at the same time to obtain RNA polymerase; and, purifying the RNA polymerase by using an adsorbent to trap the tagged RNA polymerase.

* * * * *